US008371187B2

(12) United States Patent
Payandeh et al.

(10) Patent No.: US 8,371,187 B2
(45) Date of Patent: Feb. 12, 2013

(54) SPHERICAL LINKAGE AND FORCE FEEDBACK CONTROLS

(75) Inventors: Shahram Payandeh, Coquitlam (CA); Hendrik Van der Wal, Maple Ridge (CA); Temei Li, Chung-Li (TW)

(73) Assignee: Simon Fraser University, Burnaby, British Columbia (CA)

( * ) Notice: Subject to any disclaimer, the term of this patent is extended or adjusted under 35 U.S.C. 154(b) by 1181 days.

(21) Appl. No.: 11/792,244

(22) PCT Filed: Dec. 20, 2005

(86) PCT No.: PCT/CA2005/001938
§ 371 (c)(1),
(2), (4) Date: Mar. 31, 2008

(87) PCT Pub. No.: WO2006/066401
PCT Pub. Date: Jun. 29, 2006

(65) Prior Publication Data
US 2009/0095108 A1     Apr. 16, 2009

Related U.S. Application Data

(60) Provisional application No. 60/636,864, filed on Dec. 20, 2004.

(51) Int. Cl.
*G05G 9/047* (2006.01)
*G05G 1/00* (2006.01)
(52) U.S. Cl. .................... 74/471 XY; 74/469
(58) Field of Classification Search ............... 74/469, 74/471 XY, 480 R
See application file for complete search history.

(56) References Cited

U.S. PATENT DOCUMENTS

| 5,317,301 | A | | 5/1994 | DeVolpi |
| 5,805,140 | A | * | 9/1998 | Rosenberg et al. ............ 345/161 |
| 6,024,576 | A | * | 2/2000 | Bevirt et al. ................ 434/262 |
| 6,104,382 | A | * | 8/2000 | Martin et al. ............... 345/161 |
| 6,154,198 | A | * | 11/2000 | Rosenberg ................... 345/161 |
| 6,909,205 | B2 | * | 6/2005 | Corcoran et al. .......... 310/12.14 |
| 7,204,168 | B2 | * | 4/2007 | Najafi et al. ............ 74/471 XY |
| 2005/0252329 | A1 | * | 11/2005 | Demers .................... 74/471 XY |
| 2010/0206121 | A1 | * | 8/2010 | Helmer et al. ................ 74/491 |

FOREIGN PATENT DOCUMENTS

| CA | 2 274 049 A1 | 6/1998 |
| CA | 2 305 320 A1 | 4/1999 |
| WO | WO 98/09580 | 3/1998 |

* cited by examiner

*Primary Examiner* — Justin Krause
(74) *Attorney, Agent, or Firm* — Chernoff Vilhauer McClung & Stenzel, LLP

(57) ABSTRACT

A user interface system comprises a plurality of linkages connected between a platform and a base. The linkages permit motion of the platform over at least a portion of a spherical surface. A support assembly coupled between the platform and the base comprises a spherical joint having a center of rotation substantially concentric with a center of the spherical surface. The spherical joint constrains motion of the platform to the spherical surface. The system may include a sensor corresponding to each linkage. Each sensor may be coupled to sense a movement of its corresponding linkage in response to motion of the platform over the portion of the spherical surface. A user-manipulable handle may be coupled to the platform so that the user can move the platform.

30 Claims, 12 Drawing Sheets

SPHERICAL LINKAGE AND FORCE FEEDBACK CONTROLS

RELATED APPLICATIONS

This application claims priority from U.S. application No. 60/636,864 filed 20 Dec. 2004 which is hereby incorporated herein by reference.

TECHNICAL FIELD

The invention relates to input force feedback controls. Some embodiments provide force feedback controls that include a moveable handle or other grippable member for use in input devices of user interface systems, haptic systems or the like.

BACKGROUND

Robotic systems may be controlled by corresponding user interfaces. Some user interface systems permit users to control robotic systems by manipulating an interface member (e.g. a grippable handle or the like) in space to provide control information to the robotic system. Some user interface systems allow users to manipulate virtual objects by manipulating an interface member.

In such user interface systems, it is often desirable to provide the user with force feedback. User interface systems incorporating force feedback are referred to in the art as "haptic systems" or "haptic devices". Force feedback can allow the user to experience the sensation of feeling virtual objects that the user is interacting with by way of the user interface and can provide improved user control over the forces applied by a corresponding robotic system.

There is a need for haptic user interface systems and other force feedback devices which provide force feedback to a user.

BRIEF DESCRIPTION OF THE DRAWINGS

In drawings which illustrate non-limiting embodiments of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
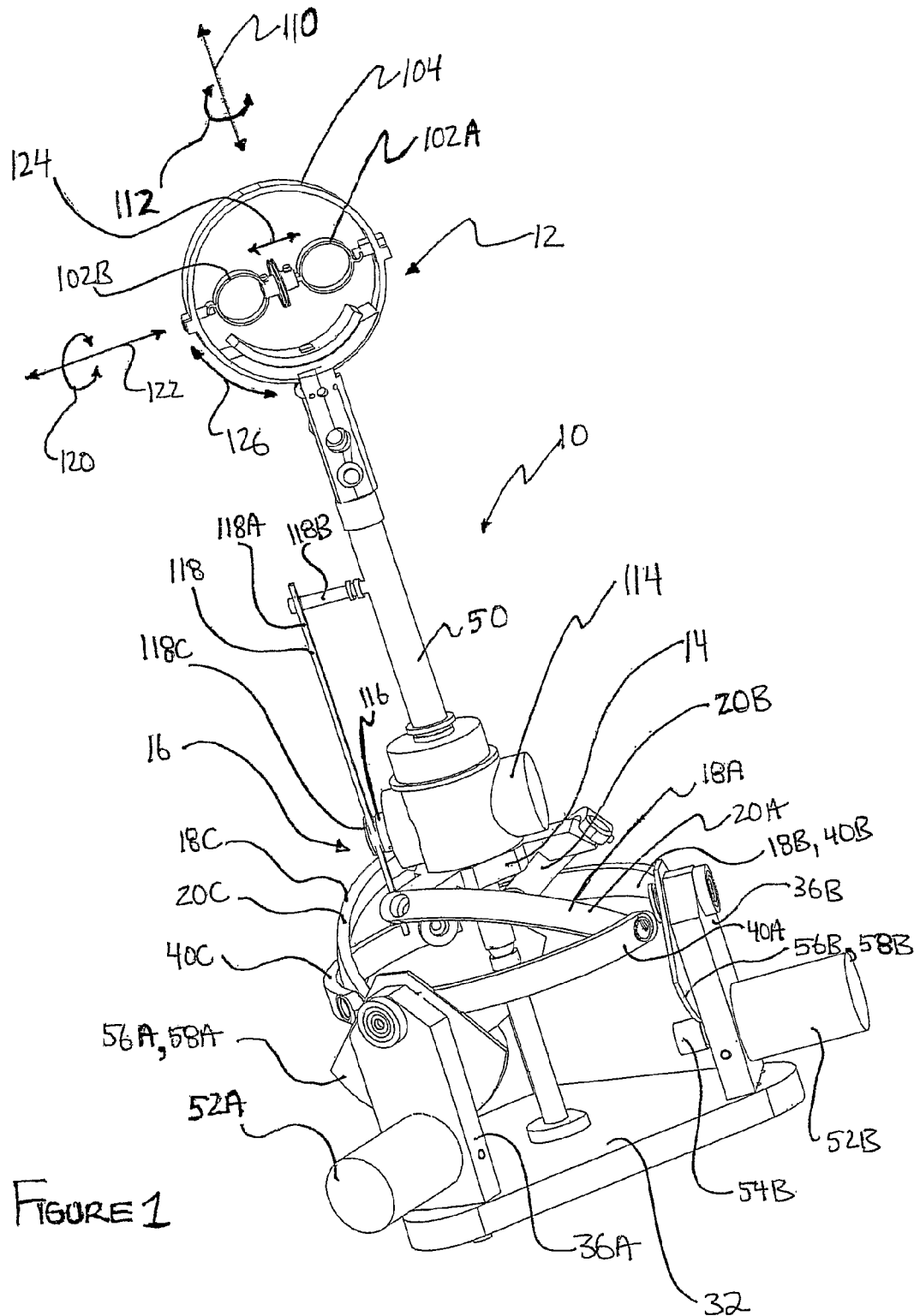
FIG. 1 is a perspective view of a force feedback device according to a particular embodiment of the invention.

FIG. 1 shows a force-feedback 10 according to an embodiment of the invention. Device 10 comprises a hand-operated handle assembly 12, which may be used by a user to interact with device 10. Handle assembly 12 is supported on a platform 14 by shaft 50. Device 10 comprises a mechanism 16 that permits platform 14 to move in multiple dimensions. In the illustrated embodiment, mechanism 16 comprises a plurality of linkages 18A, 18B, 18C (collectively, linkages 18) which allow platform 14 to be moved over a portion of a surface of an imaginary sphere centred at point 28A. Mechanism 16 provides platform 16 with three degrees of freedom q, f, y shown in FIG. 1A.

Figure 2:
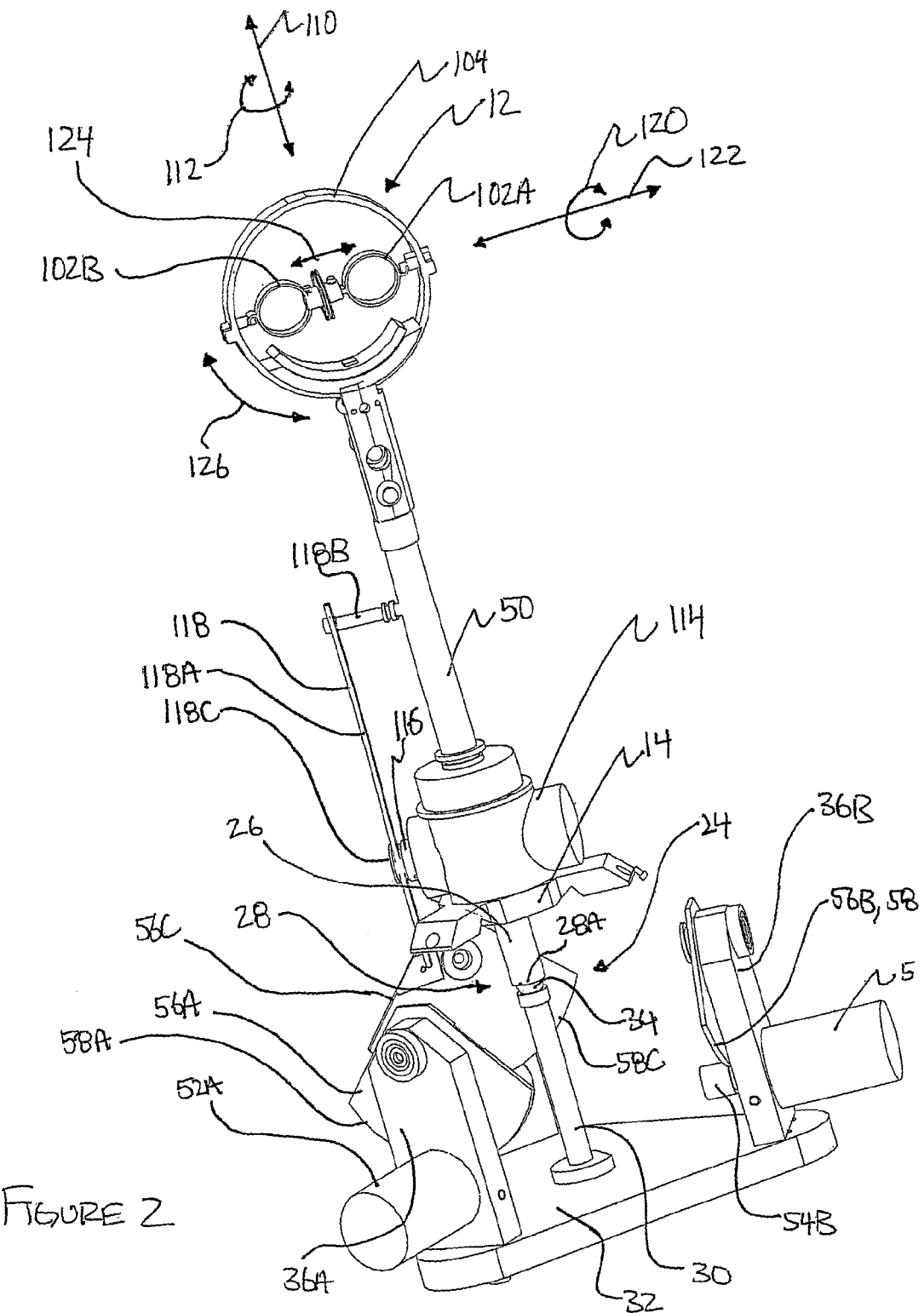
FIG. 2 is another perspective view of the FIG. 1 device with its linkages removed to provide a better view of its support.

FIG. 2 shows the FIG. 1 device 10 without linkages 18. Device 10 comprises a support assembly 24 which, in the FIG. 2 embodiment, extends between base surface 32 and platform 14 to support platform 14. In device 10, base surface 32 is provided by base member 31. In some embodiments, base member 31 is not required and base surface 32 may be the surface on which device 10 is standing. Base surface 32 may be relatively flat.

Support assembly 24 comprises a support joint 28 between support members 26, 30. Support joint 28 is a spherical joint having a centre of rotation 28A. The center of rotation 28A of spherical joint 28 is concentric with the sphere about which mechanism 16 permits movement of platform 14. In device 10, spherical support joint 28 incorporates a ball 34 between support members 26, 30 and support members 26, 30 have corresponding concave sockets (not visible) which allow support members 26, 30 to move independently relative to ball 34. A portion of each of the concave sockets of support members 26, 30 may be spherically concave with a radius of curvature that is substantially similar to that of ball 34, such that spherical support joint 28 resists motion of support members 26, 30 in a radial direction relative to centre of rotation 28A.

In other embodiments, a first one of support members 26, 30 is fixed relative to ball 34 and need not incorporate a concave socket. In such embodiments, the second one of support members 26, 30 incorporates a concave socket for movement relative to ball 34. A portion of the concave socket on the second one of support members 26, 30 may be spherically concave with a radius of curvature that is substantially similar to that of ball 34. In other embodiments, spherical support joint 28 is implemented without ball 34. In such embodiments, a first one of members 26, 30 comprises a convex surface and the other one of members 26, 30 comprises a concave socket. A portion of the convex surface may be spherically convex and a portion of the concave socket may be spherically concave with substantially similar radii of curvature.

As used herein, the term "spherical joint" (including "spherical support joint") means a joint which facilitates movement of at least one element such that a point within the element moves over at least a portion of a spherical surface that is centred at a centre of rotation and wherein the joint resists movement of the point in a radial direction relative to the centre of rotation. Together, mechanism 16 and spherical joint 28 permit platform 14 to move about the surface of an imaginary sphere having a radius r (FIG. 1A) centred at the centre of rotation 28A of spherical support joint 28 (i.e. platform 14 is permitted to move in the angular directions $\theta$, $\phi$, $\psi$ of FIG. 1A). Spherical joint 28 constrains the motion of platform 14 to this spherical surface by resisting movement of platform 14 in a radial direction relative to centre of rotation 28A. During movement of platform 14, support member 26 moves relative to support member 30 such that platform 14 remains a fixed distance r from the centre of rotation 28A of spherical support joint 28. Preferably, spherical support joint 28 provides minimal resistance to movement of platform 14 in the angular directions $\theta$, $\phi$, $\psi$. As explained in more detail below, support 24 and spherical support joint 28 prevent mechanism 16 and linkages 18 from binding and allow system 10 to provide a user with improved force feedback.

Figure 3A:
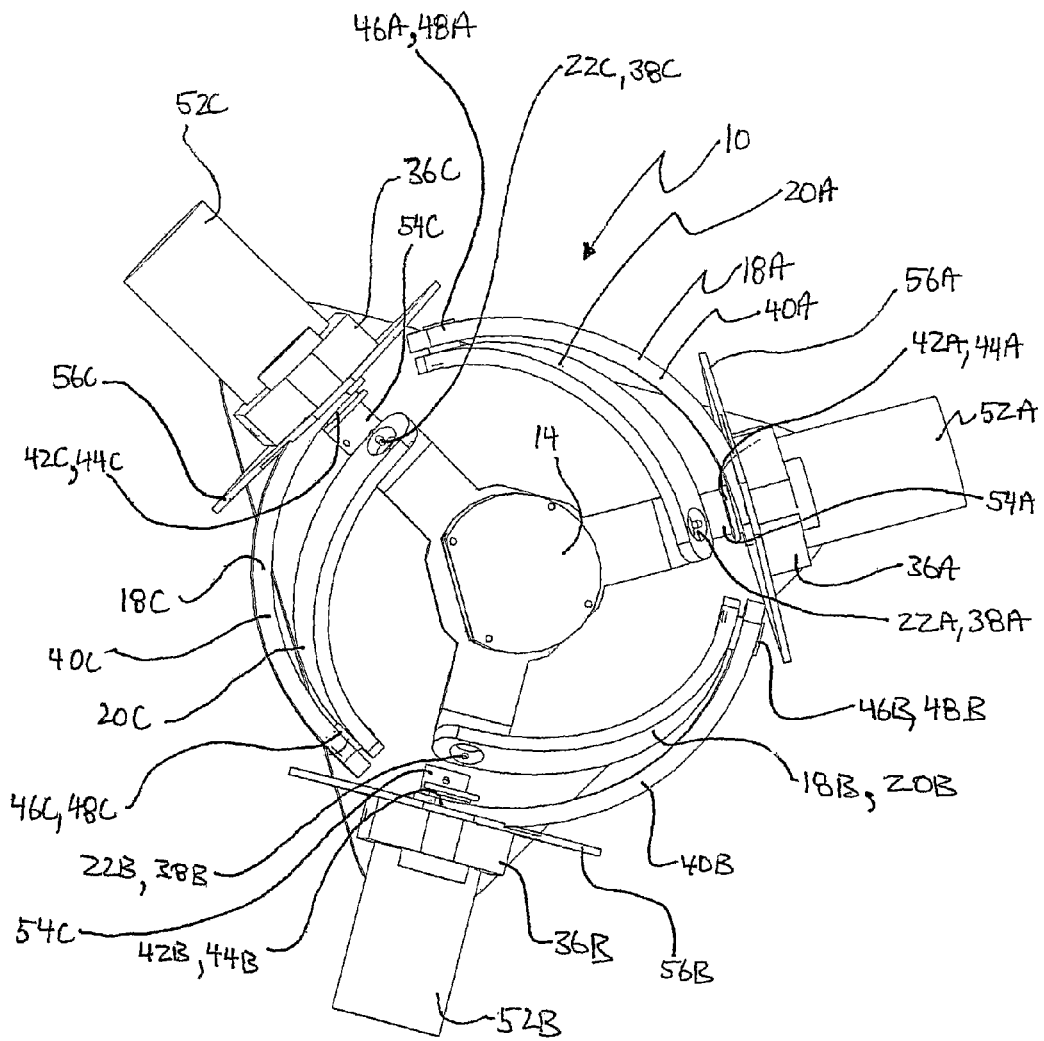
FIG. 3A is an overhead view of the FIG. 1 device with its handle assembly removed to provide a better view of its linkages.

FIG. 3A shows an overhead view of system 10 with handle assembly 12 and some of its other components removed. As shown in FIG. 3A, mechanism 16 incorporates linkages 18 which moveably couple platform 14 to mounts 36A, 36B, 36C (collectively, mounts 36). Mounts 36 may optionally be rigidly connected to base surface 32. Each of linkages 18 comprises a pair of links, which include:

primary links 20A, 20B, 20C (collectively, primary links 20) pivotally coupled to platform 14 at primary pivot joints 22A, 22B, 22C (collectively, primary pivot joints 22) for pivotal movement about primary pivot axes 38A, 38B, 38C (collectively, primary pivot axes 38); and secondary links 40A, 40B, 40C (collectively, secondary links 40) pivotally coupled at their first ends to mounts 36 at pivot joints 42A, 42B, 42C (collectively, secondary pivot joints 42) for pivotal movement about secondary pivot axes 44A, 44B, 44C (collectively, secondary pivot axes 44) and at their second ends to primary links 20 at intermediate pivot joints 46A, 46B, 46C (collectively, intermediate pivot joints 44) for pivotal movement about intermediate pivot axes 48A, 48B, 48C (collectively, intermediate pivot axes 48).

In system 10, primary pivot axes 38, secondary pivot axes 44 and intermediate 25 pivot axes 48 intersect at point 28A (i.e. the centre of rotation 28A of spherical support joint 28). As platform 14 moves about a portion of an imaginary spherical surface centred at point 28A (i.e. in the angular directions $\theta$, $\phi$, $\psi$ of FIG. 1A), primary links 20 and secondary links 40 pivot to different orientations about primary pivot axes 38, secondary pivot axes 44 and intermediate pivot axes 48. In system 10, 30 mechanism 16 may operate such that regardless of the configuration of linkages 18, a radial line r (FIG. 1A) extending between central point 28A and platform 14 that intersects platform 14 at a particular location will pass through platform 14 with the same orientation.

Handle assembly 12 is mounted on platform 14 via shaft 50. A user may exert force on platform 14 through handle assembly 12. Such force may generally be oriented in any direction and may cause movement of platform 14 in the angular directions $\theta$, $\phi$, $\psi$ as discussed above. In response to such applied force, the corresponding movement of mechanism 16 will typically require the simultaneous movement of a number of pivot joints 22, 42, 46 (i.e. unless the applied force happens to be oriented to coincide exactly with pivotal movement of one of pivot joints 22, 42, 46). In addition, applied force may tend to move platform 14 off of the spherical surface over which mechanism 16 permits movement. In such circumstances (i.e. under a load which has a tendency to cause simultaneous movement of a number of pivot joints 22, 42, 46 and/or under a load which tends to move platform 14 off of the spherical surface over which mechanism 16 permits movement), mechanism 16 may be susceptible to binding at one or more of pivot joints 22, 42, 46.

Support assembly 24 acts to counter force applied in a radial direction (relative to centre of rotation 28A) and to constrain the motion of platform 14 to the angular directions $\theta$, $\phi$, $\psi$, thereby reducing the chance that one or more of linkages 18 will bind at pivot joints 22, 42, 46. Since spherical support joint 28 is also capable of facilitating relative movement of support member 26 in any direction that platform 14 is capable of moving (i.e. in the angular directions $\theta$, $\phi$, $\psi$), spherical support joint 28 is unlikely to bind under the application of force.

For each linkage 18 in mechanism 16, system 10 comprises a corresponding motor 52A, 52B, 52C (collectively, motors 52) or some other suitable actuator and a corresponding sensor 54A, 54B, 54C (collectively, sensors 54). Motors 52 are operationally coupled to secondary pivot joints 42 to apply torques which would tend to pivot secondary links 40 about secondary axes 44. In system 10, motors 52 are operationally coupled to secondary pivot joints 42, via sectors 56A, 56B, 56C (collectively, sectors 56) which are coupled to pivot with secondary links 40. Sectors 56 have corresponding arcuate sides 58A, 58B, 58C (collectively, arcuate sides 58) which are operationally connected to the shafts (not shown) of motors 52. Sectors 56 (may be coupled to the shafts of motors 52 by suitable gear mechanisms, pulley and cable mechanisms, friction-based mechanisms or the like. In a particular embodiment, tendons (not shown) are wrapped around the shafts of motors 52 (or around pulleys coupled to move with the shafts of motors 52) and are rigidly connected to sectors 56, such that movement of the shafts of motors 52 causes the tendons to pull on sectors 56 and causes corresponding pivotal motion of secondary links 40 (and pivot joints 42) about secondary axes 44.

Sensors 54 are connected to detect the angular positions of secondary links 40 about secondary axes 44. Sensors 54 may be connected to the shafts of motors 52 or to other components in the operative connection between the shafts of motors 52 and secondary pivot joints 42. Sensors 54 may comprise rotary encoders. Motors 52 and sensors 54 may respectively comprise the motor and sensor components of servomotors. A computer or other processing device (e.g. processor 712 of FIG. 8 discussed in more detail below) may be connected to receive position signals from sensors 54 (i.e. signals corresponding to the positions of secondary links 40 about secondary axes 44). When a user moves handle assembly 12 and causes corresponding movement of platform 14 in the angular directions $\theta$, $\phi$, $\psi$, the processor may use the position signals from sensors 54 to determine drive signals for motors 52 to provide the user with force feedback.

Those skilled in the art will appreciate that there are a wide variety of ways in which a motor can be operationally coupled to drive a component about a pivot axis implemented by a pivot joint and to provide a corresponding sensor for detecting the angular position of the component about the pivot axis. The invention should be understood to accommodate any suitable mechanism(s) for operationally coupling motors 52 to secondary links 40 or to pivot joints 42 so as to drive secondary links 40 about pivot axes 44 and any suitable arrangement for coupling a sensor to detect the motion of secondary links 40 or pivot joints 42 about pivot axes 44.

When device 10 is used to provide force feedback as a part of a haptic system, it is desirable for device 10 to be transparent to the user, such that the user can use handle assembly 12 to move platform 14 in the angular directions θ, φ, ψ and experience a feeling of force-feedback through handle assembly 12 that is independent of the mechanism 16 used to facilitate movement of platform 14. When using a transparent force feedback device, a user will not feel reaction forces from friction and inertia of the device (e.g. the components of mechanism 16) and will only feel the forces applied by the force feedback actuators (e.g. motors 52). A force feedback device with a high degree of transparency may be referred to as a high fidelity force feedback device.

Clearly, if mechanism 16 binds when handle assembly 12 is operated by a user, then device 10 is not acting in a transparent manner. As discussed above, support assembly 24 (including spherical support joint 28) reduce the chances that mechanism 16 will bind during movement of platform 14, thereby improving the fidelity of device 10. Support 24 (and spherical support joint 28) also improve the fidelity of device 10 by reducing the friction, deadweight and inertia in mechanism 16 (i.e. in links 20, 40 and pivot joints 22, 42, 46). In some embodiments, linkages 18 can be made from lighter materials, since linkages 18 are not required to support platform 14 against forces applied by a user in the radial direction. The reduction in friction, deadweight and inertia of mechanism 16 improve the ability of a user to manipulate platform 14 via handle assembly 12 (i.e. movement of mechanism 16 will be more responsive (e.g. in speed and accuracy) to forces applied by the user). In addition, the reduction in friction, deadweight and inertia of mechanism 16 improve the ability of motors 52 or provide force feedback to a user (i.e. movement of mechanism 16 will be more responsive (e.g. in speed and accuracy) to forces applied by motors 52).

The dimensions of device 10 (and in particular the dimensions of mechanism 16) maybe selected to provide sufficient strength while permitting platform 14 to be moved through the desired range of angles θ, φ, ψ.

Handle assembly 12 of device 10 comprises finger grips 102A, 102B (collectively, finger grips 102) through which a user may insert their fingers to manipulate device 10. Finger grips 102 are supported by ring 104. Using finger grips 102, a user may manipulate platform 14 in the angular directions θ, φ, ψ as discussed above.

Figure 3B:
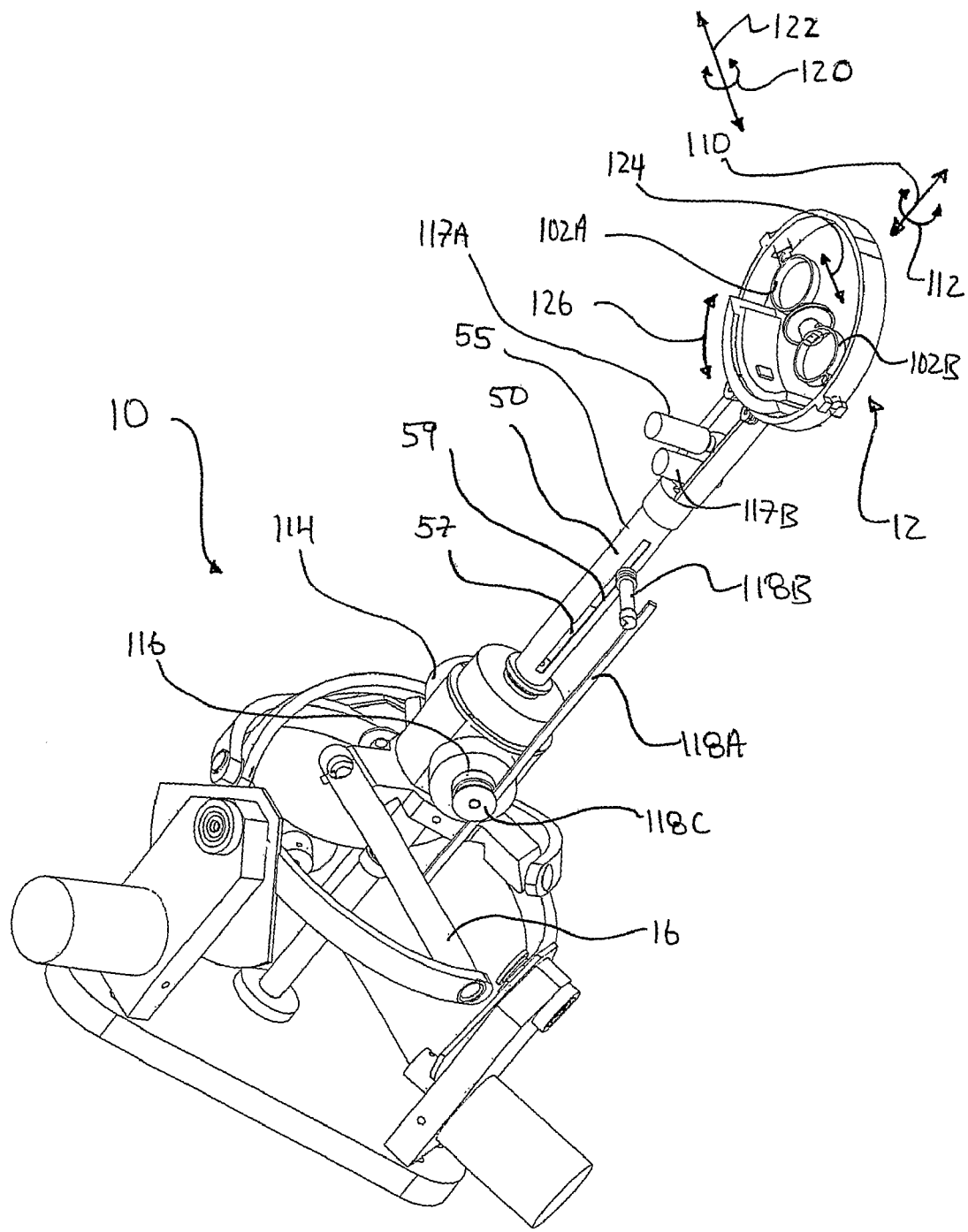
FIG. 3B is another perspective view of the FIG. 1 device from a different orientation.

As shown most clearly in FIGS. 2 and 3B, handle assembly 12 may provide device 10 with a number of additional degrees of freedom. Using finger grips 102, a user may cause handle assembly 12 to move inwardly and outwardly along the longitudinal shaft axis (as indicated by double-headed arrow 110) of shaft 50. In device 10, handle assembly 12 is mechanically coupled to a motor 114 (or other actuator) by linkage 118 and sensor 116 is provided to detect the position of handle assembly 12 along longitudinal shaft axis 110. In this manner, a processor can receive position information from sensor 116 and can drive motor 114 to provide the user with force feedback that counters the movement of handle assembly 12 in either direction along longitudinal shaft axis 110.

As shown best in FIG. 3B, shaft 50 of device 10 comprises: an exterior shaft member 55; a slot 57 which runs along the longitudinal dimension of exterior shaft member 55; and an interior shaft member 59 which is slidably moveable within exterior shaft member 55 along longitudinal shaft axis 110. Handle assembly 12 is coupled to move with interior shaft member 59 along longitudinal shaft axis 110.

In device 10, linkage 118 which couples handle assembly 12 to motor 114 comprises a longitudinal shaft coupling arm 118A which extends in a direction substantially parallel to shaft 50. Transverse shaft coupling arm 118B connects longitudinal shaft coupling arm 118A (through slot 57) to interior shaft member 59.

Motor engaging component 118C is coupled between motor 114 and longitudinal shaft coupling arm 118A so as to transfer torque from motor 114 to shaft coupling arm 118A and to thereby apply linear force to handle assembly in one of the directions of longitudinal shaft axis 110. In some embodiments, the coupling between shaft coupling arm 118A and motor engaging component 118C is implemented with a friction coupling. In other embodiments, shaft coupling arm 118A and motor engaging component 118C may comprise pulleys and cables, gears or the like. In one particular embodiment a tendon (not shown) is wrapped around the shaft of motor 114 (or around a pulley coupled to move with the shaft of motor 114) and is rigidly coupled to shaft coupling arm 118A, such that movement of the shaft of motor 114 causes the tendon to pull on shaft coupling arm 118A and causes corresponding translational motion of handle assembly 12 along the longitudinal shaft axis 110.

Those skilled in the art will appreciate that there are a wide variety of ways in which a motor can be operationally coupled to drive a component in a translational manner and to provide a corresponding sensor for detecting the translational position of the component. The invention should be understood to accommodate any suitable mechanism(s) for operationally coupling a motor 114 to exert force on handle assembly 12 in the direction of longitudinal shaft axis 110 and any suitable arrangement for coupling a sensor to detect the motion of handle assembly 12.

Handle assembly 12 may provide other degrees of freedom. By way of non-limiting example: a user may pivot finger grips 102 and ring 104 about the longitudinal axis 110 of shaft 50 as indicated by double-headed arrow 112; a user may pivot finger grips 102 relative to ring 104 about axis 122 as indicated by double-headed arrow 120; a user may move finger grips 102 toward one another and/or away from one another as indicated by double-headed arrow 124; and a user may pivot finger grips 126 within ring 104 as indicated by double-headed arrow 126.

Each of these movements of handle assembly 12 may be facilitated by a suitably configured mechanical joint (not shown), such as a pivot joint or a suitably configured mechanism (not shown) capable of providing translational movement, for example. Sensors (not shown) may be connected to detect the configuration of these joints and/or mechanisms (e.g. the pivotal orientation of a pivot joint and/or the translational orientation of a translation mechanism). Motors or other actuators (e.g. motors 117A, 117B) may be operationally coupled to pivot and/or translate finger grips 102 and/or ring 104 using these joints and/or mechanisms. A computer or other processor can receive position information from the sensors and use the motors to provide the user with force feedback through these joints and/or mechanisms.

Figure 4A:
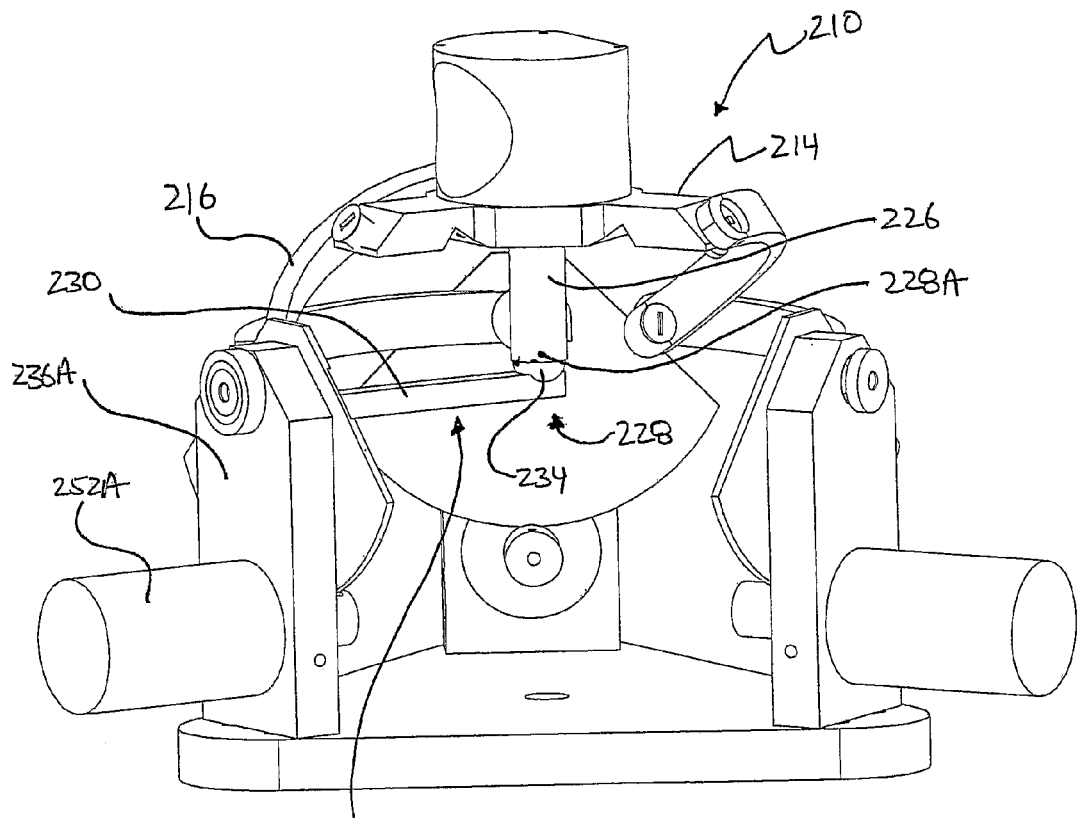
FIG. 4A is a partial perspective view of a force feedback device according to another embodiment of the invention incorporating a spherical support joint with a different support assembly.

Spherical support joint 28 may generally be supported using any suitable support assembly. In device 10, spherical support joint 28 is supported on the end of a centrally-located, vertically-extending support member 30. FIG. 4A is a partial view of a force feedback device 210 according to another embodiment of the invention. Some of the components of device 210 are not shown in FIG. 4A to provide a view of support assembly 224, wherein ball 234 of spherical support joint 228 is supported by an arm 230 that is cantilevered from mount 236A. In other respects, spherical support joint 228 is similar to spherical support joint 28 of device 10. Device 210 incorporates a mechanism 216 (similar to mechanism 16 of device 10) which permits platform 214 to be moved about an imaginary spherical surface.

As with device 10, the spherical support joint 228 of device 210 is located such that its centre of rotation is coincident with the centre of the imaginary sphere about which platform 14 can move (i.e. the point of intersection of the primary, secondary and intermediate axes of mechanism 216. Spherical support joint 228 may act in a manner substantially similar to spherical support joint 28 of device 10 to prevent binding of mechanism 216 and to reduce the friction, deadweight and inertia of mechanism 216, thereby improving the fidelity of the force feedback provided by device 210.

Figure 4B:
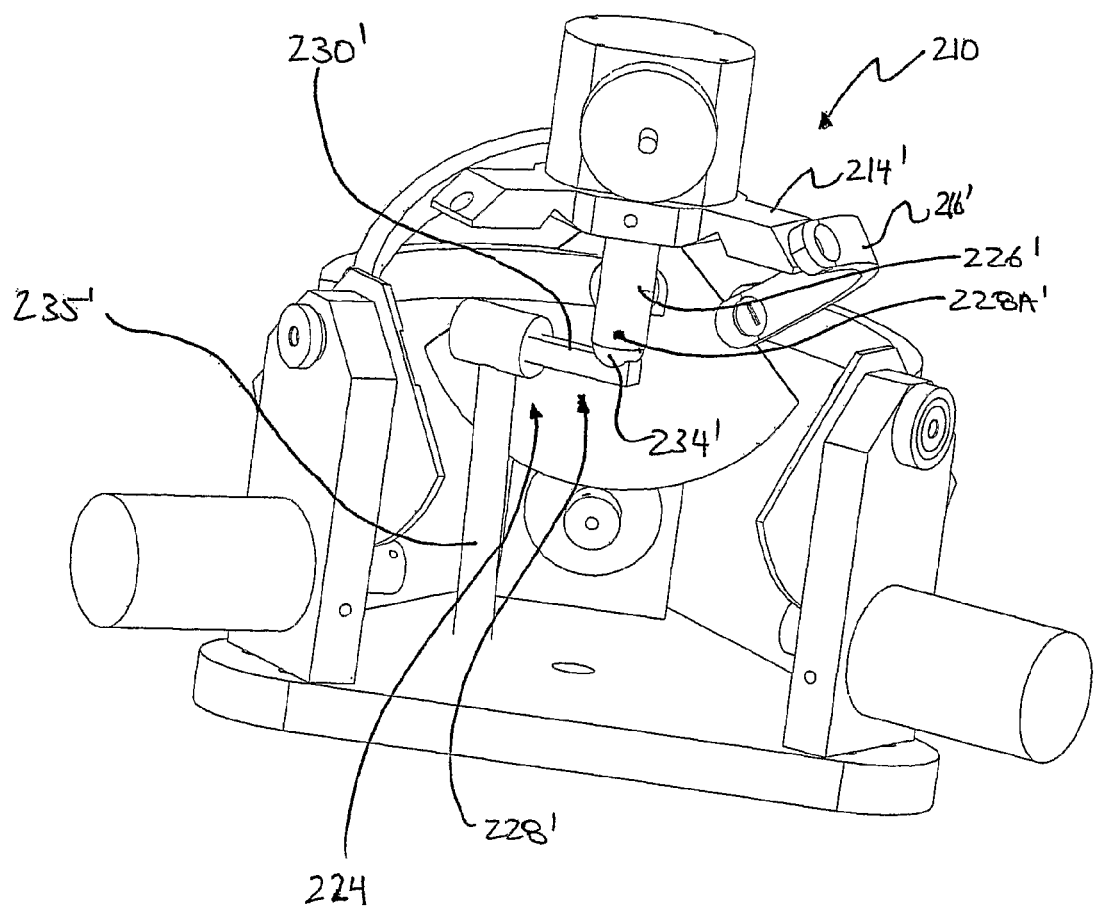
FIG. 4B is a partial perspective view of a force feedback device according to another embodiment of the invention incorporating a spherical support joint with a different support assembly.

It is not generally necessary that arm 230 of spherical support joint 228 be cantilevered from the same mount 236A that holds motor 252A. FIG. 4B shows a device 210' according to another embodiment of the invention. Some of the components of device 210' are not shown in FIG. 4A to provide a view of support assembly 224', wherein ball 234' of spherical support joint 228' is supported by an arm 230' that is cantilevered from its own mount 235'.

Those skilled in the art will appreciate that there are other arrangements for supporting a spherical support joint with its centre of rotation located at the intersection of the primary axes 38, secondary axes 44 and intermediate axes 48. Preferably, the structure provided to support the spherical support joint does not unduly limit the range of motion of platform 14 by interfering with mechanism 16.

Figure 5:
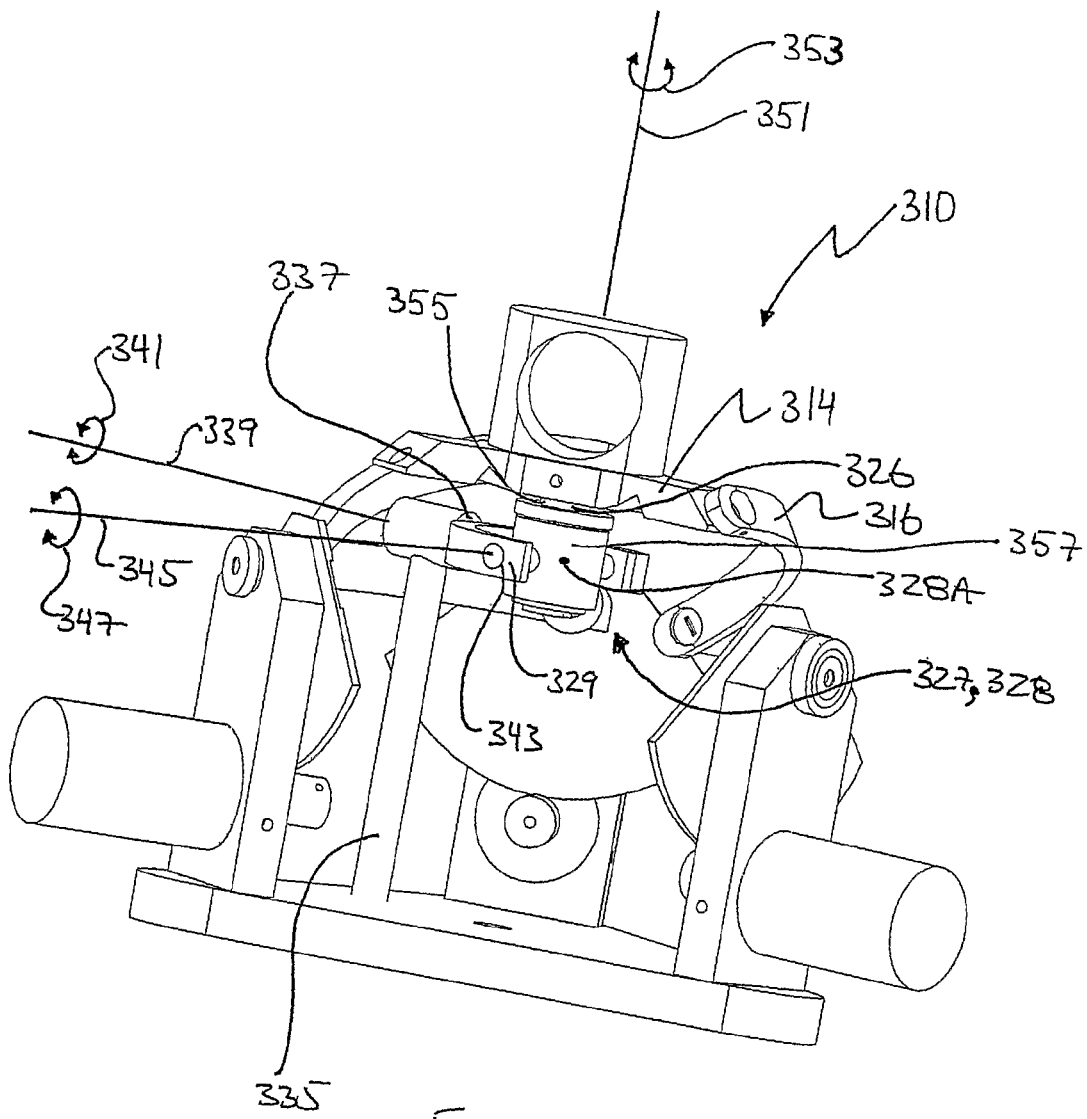
FIG. 5 is a partial perspective view of a force feedback device according to another embodiment of the invention wherein the spherical support joint comprises a 3-DOF.

Spherical support joint 28 maybe implemented using other constructions. In device 10, spherical support joint 28 is implemented using a ball 34 and at least one support member with a concave socket (i.e. a ball and socket construction). FIG. 5 is a partial view of a force feedback device 310 according to another embodiment of the invention. Some of the components of device 310 are not shown in FIG. 5 to provide a view of spherical support joint 328 which comprises a three degree of freedom (3-DOF) joint 327. 3-DOF joint 327 comprises: an optional support member 326 that is rigidly connected to platform 314; a joint body 357 that is pivotally coupled to support member 326 (or to platform 314) at a first pivot joint 355 for relative pivotal movement between support member 326 (or platform 314) and joint body 357 about a first pivot axis 351 as indicated by double-headed arrow 353; a second pivot joint 343 for relative pivotal movement between joint body 357 and support member 329 about a second pivot axis 345 as indicated by double-headed arrow 347; and a third pivot joint 337 for relative pivotal movement between joint body 357 and support member 335 about a third pivot axis 339 as indicated by double-headed arrow 341.

In the illustrated embodiment, 3-DOF joint 327 is configured such that pivot axes 339, 345, 351 are orthogonal to one another and is located such that pivot axes 339, 345, 351 intersect at point 328A, which is the centre of the sphere about which mechanism 316 permits movement (i.e. the same point 328A of intersection of the primary, secondary and intermediate axes of mechanism 316). Together, 3-DOF joint 327 and mechanism 316 permit the movement of platform 314 in the angular directions θ, φ, ψ about an imaginary sphere having a radius r and centred at point 328A. 3-DOF joint 327 has the characteristics of a spherical support joint discussed above. More specifically, 3-DOF joint 327 constrains movement of platform 314 such that platform 314 is able to move over at least a portion of a spherical surface that is centred at a centre of rotation 328A is prevented from moving in a radial direction relative to the centre of rotation 328A.

In a manner similar to that in which ball and socket joint 28 (together with supports 26, 30) support mechanism 16 (FIGS. 1-3B), 3-DOF joint 327 (together with support members 326, 329, 335) support mechanism 316 to reduce the chances of mechanism 316 binding and to reduce the friction, deadweight and inertia of mechanism 316. 3-DOF joint 327 provides the additional feature that longitudinal shaft 350 which connects handle assembly 312 to platform 314 can project through platform 314 and through the centre of rotation 328A.

Handle assembly 12 may be implemented using other alternative handle apparatus. As explained above, in device 10 of FIGS. 1-3B, handle assembly 12 comprises a pair of finger grips 102 housed within a ring 104, which permits finger grips 102 to move with a number of additional degrees of freedom (i.e. about the longitudinal shaft axis 110 (double-headed arrow 112); about axis 122 (double-headed arrow 120); toward one another and/or away from one another (double-headed arrow 124); and within ring 104 (double-headed arrow 126)).

Figure 6A:
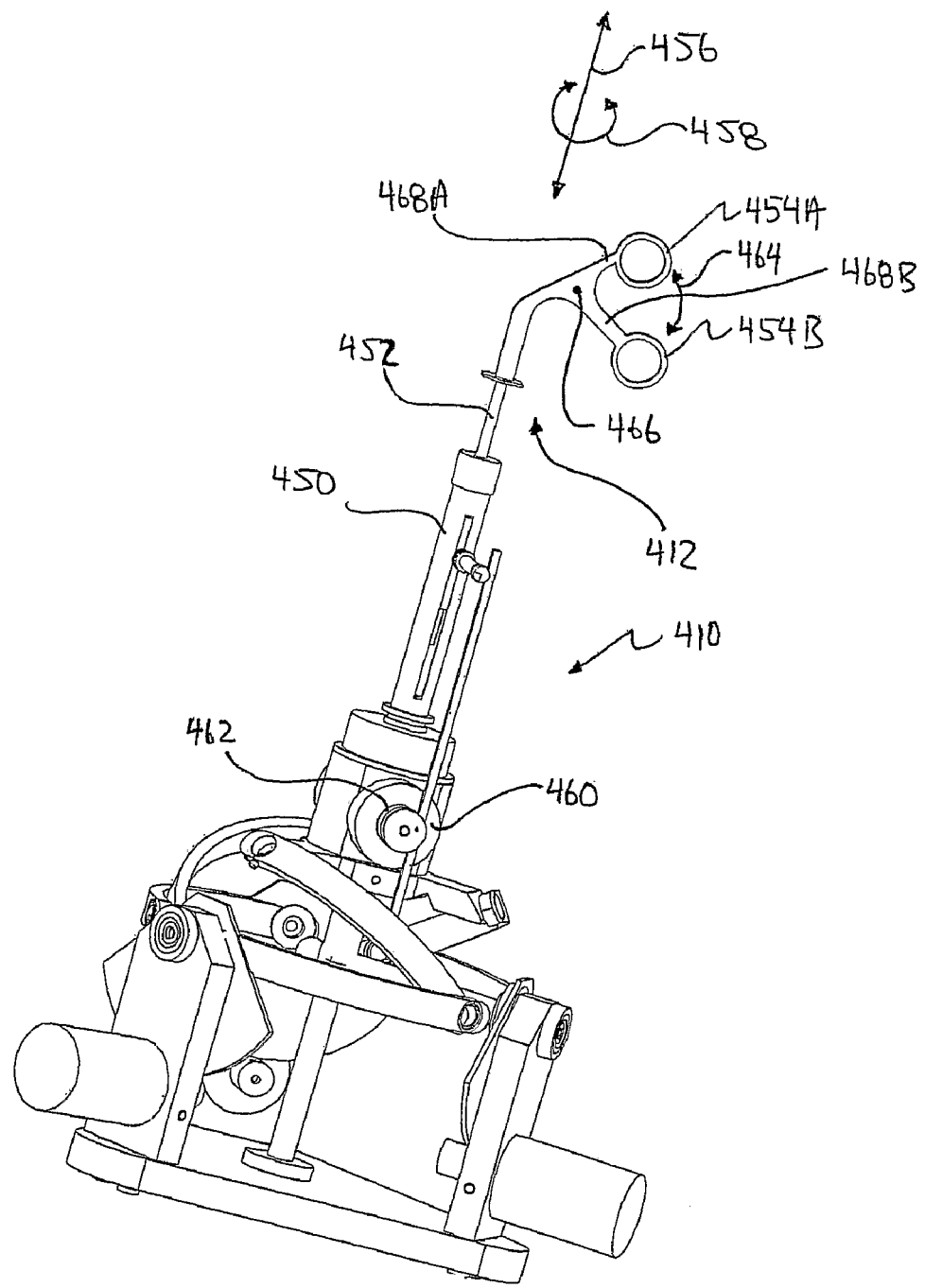
FIG. 6A is a perspective view of a force feedback device according to another embodiment of the invention having a different handle assembly.
Figure 6K:
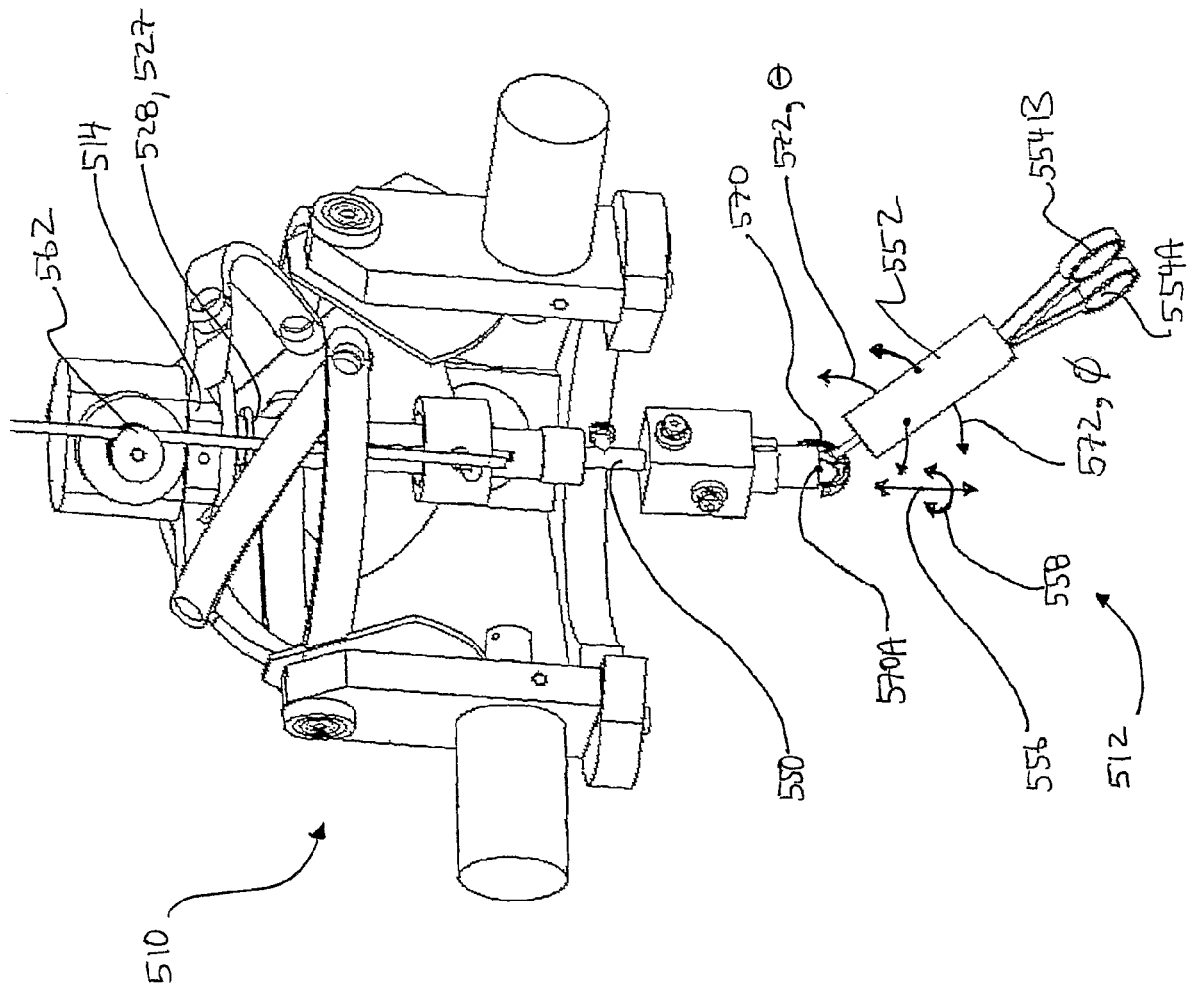
FIG. 6B is a perspective view of a force feedback device according to another embodiment of the invention having another different handle assembly and having a spherical support joint located between its platform and its handle assembly.

FIG. 6A depicts a force feedback device 410 according to another embodiment of the invention wherein handle assembly 412 comprises a handle member 452 having a pair of finger grips 454A, 454B (collectively, finger grips 454) that are fixed relative to one another. In device 410, handle member 452 may move backward and forward along the direction of the longitudinal axis (as indicated by double-headed arrow 456) of shaft 450 and may pivot about the longitudinal axis 456 of shaft 450 (as indicated by double-headed arrow 458).

Device 410 incorporates a sensor 462 connected to detect the position of handle member 452 along longitudinal shaft axis 456 and to provide this position information to a processor. Device 410 also incorporates a motor 460 (or other actuator) operationally coupled to drive handle member 452 along longitudinal shaft axis 456 to provide force feedback to handle member 452. The operation of sensor 462 and motor 460 may be substantially similar to motor 114 and sensor 116 of device 10 (FIGS. 1-3B). Device 410 may also incorporate one or more sensors (not shown) for detecting the pivotal orientation of handle member 452 about longitudinal shaft axis 456 and one or more actuators (not shown) operationally coupled to handle member 452 for providing force feedback to the movement of handle member 452 about longitudinal shaft axis 456. A computer or other processor (not shown) may be used to receive position information from the sensors and to provide drive signals to the motors (or other actuators).

In other embodiments, handle assembly 412 may incorporate one or more additional pivot joints (not shown) which permit one or both of finger grips 454 to move toward or away from one another as indicated by double-headed arrow 464. The one or more additional pivot joints may be located at the junction 466 of arms 468A, 468B for example. The one or more pivot joints may also be provided with one or more suitably connected sensors and one or more suitably connected actuators which permit force feedback to the movement of finger grips 454 toward and/or away from one another.

FIG. 6B depicts a force feedback device 510 according to another embodiment of the invention. Device 510 differs from the previously described embodiments in that device 510 comprises a spherical support joint 528 that is located between platform 514 and handle assembly 512. In the illustrated embodiment, spherical support joint 528 of device 510 comprises a 3-DOF joint 527 (similar to 3-DOF joint 327 of device 310 (FIG. 5)), such that shaft 550 of handle assembly 512 is capable of projecting through spherical support joint 528.

Handle assembly 512 of device 510 comprises a handle member 552 having a pair of finger grips 554A, 554B (collectively, finger grips 554). Handle member 552 is coupled to shaft 550 via a secondary joint 570. Secondary joint 570 permits movement of handle member 552 relative to shaft 550 in the orthogonal angular directions θ and φ indicated by double-headed arrows 572 and 574. The movement of handle member 552 provided by secondary joint 570 may be similar to that of a joystick. Device 510 may comprise one or more sensors (not shown) connected to detect the angular position of handle member 552 relative to secondary joint 570 and/or shaft 550 and one or more motors or other actuators (not shown) operationally coupled to handle member 552 to provide force feedback to the motion of handle member 552 in the angular directions θ and φ indicated by double-headed arrows 572 and 574.

In the embodiment illustrated in FIG. 6B, finger grips 554 are rigidly coupled to handle member 552. In other embodiments, one or both of finger grips 554 may be coupled to one or more pivot joints for pivotal movement relative to handle member 552 and/or relative to the other one of finger grips 554. One or more suitably connected sensors and actuators may be connected to provide force feedback to such pivot joints. As with the previously described embodiments, handle assembly 512 maybe translated in either direction along longitudinal shaft axis 556 and maybe pivoted about longitudinal shaft axis 56 in the directions indicated by double-headed arrow 558. One or more suitably connected sensors and actuators may be connected to provide force feedback to such translation of handle assembly 512 and to such pivotal movement of handle assembly 552.

Figure 1A:
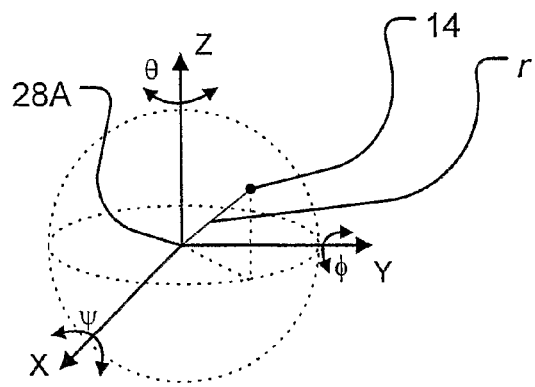
FIG. 1A is a schematic depiction showing the angular directions in which the platform of the FIG. 1 device is capable of moving.
Figure 7A:
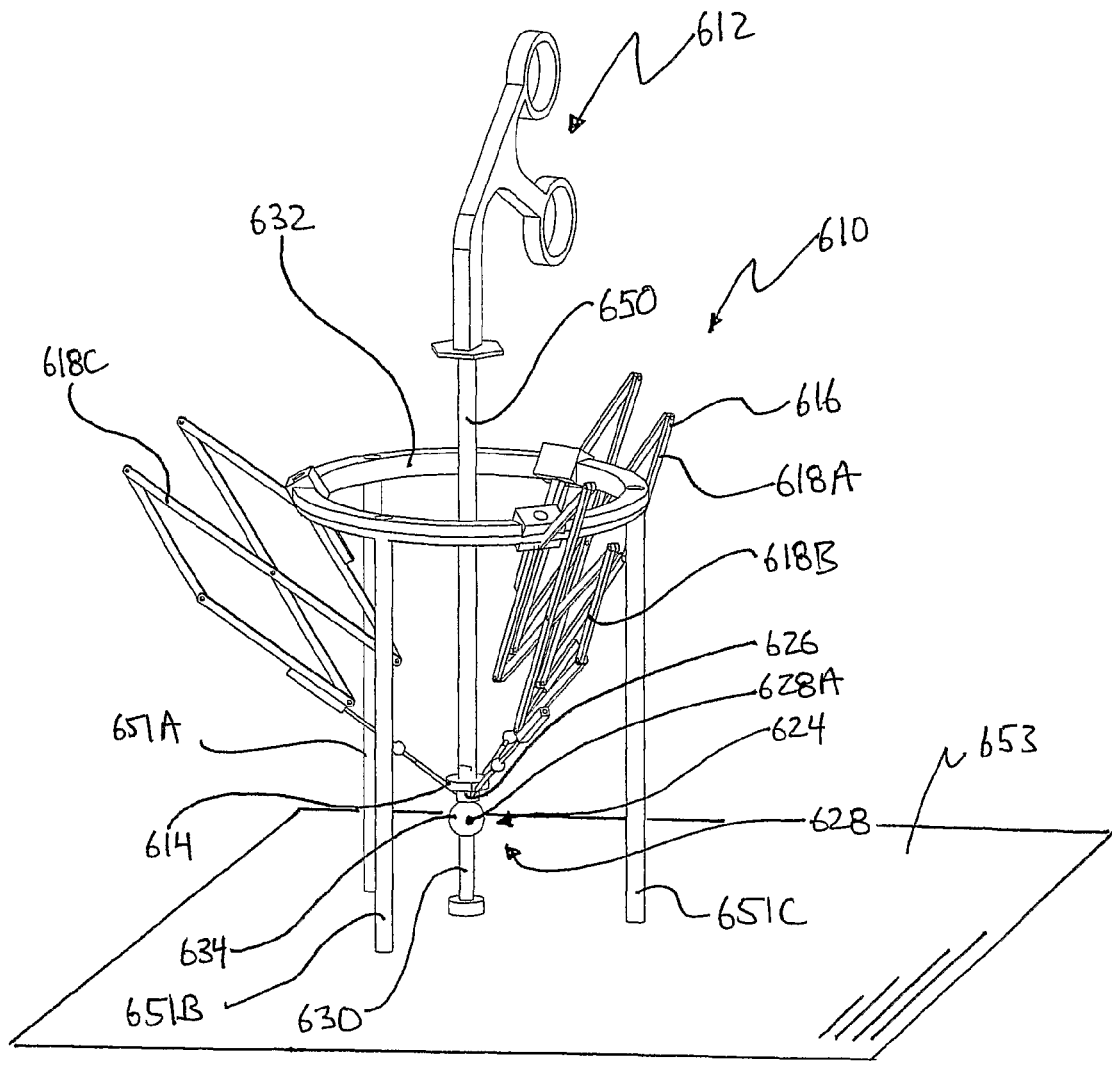
FIG. 7A is a partial perspective view of a force feedback device according to another embodiment of the invention having a different mechanism for permitting movement of the platform.

Mechanisms different from mechanism 16 maybe used to permit movement of platform 14 in the angular directions θ, φ, ψ (FIG. 1A). FIG. 7A depicts a partial view of a force feedback device 610 according to another embodiment of the invention. Device 610 comprises a different mechanism 616 for facilitating movement of platform 614 in the angular directions θ, φ, ψ (i.e. about the x, y and z axes of FIG. 1A), with an origin corresponding to the centre 628A of a spherical support joint 628. Spherical support joint 628 constrains the movement of platform 614 to the surface of an imaginary sphere centred at centre of rotation 628A. Some of the components of device 610 (e.g. sensors) are not shown in FIG. 7A to provide a better view of mechanism 616.

Mechanism 616 of device 610 comprises three linkages 618A, 61813, 618C (collectively, linkages 618) which are coupled to holding mount 632 at one of their ends and to platform 614 at their opposing ends. In device 610, linkages 618 are coupled to holding mount 632 and to platform 614 at evenly angularly-spaced apart locations (i.e. 120° apart). Linkages 618 each comprise six links interconnected by a plurality of in-plane pivot joints to provide a spherical mechanism 616. Mechanism 616 provided by linkages 618 permits platform 614 to be moved (via user actuation of handle 612) in the angular directions θ, 100, ψ (i.e. about the x, y and z axes of FIG. 1A) with an origin corresponding to the centre of rotation 628A of spherical support joint 628.

Figure 7B:
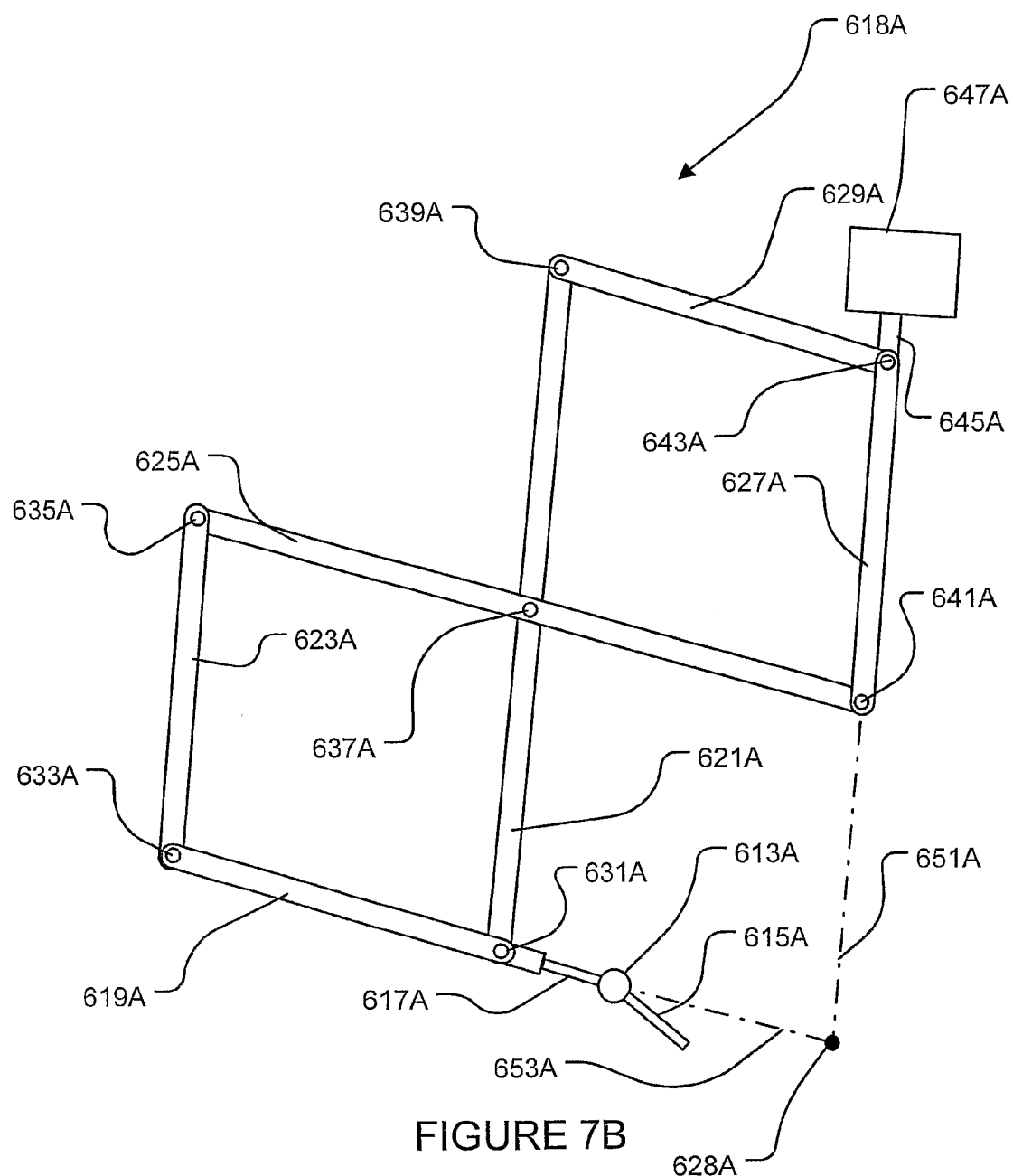
FIG. 7B is a plan view of one of the linkages of the mechanism used in the FIG. 7A device.

FIG. 7B depicts linkage 618A in more detail. It will be appreciated that linkages 618B, 618C are substantially similar to linkages 618A. Linkage 618A comprises a rod 615A which is rigidly coupled at one of its ends to platform 614 (not shown in FIG. 7B) and at its opposing end to spherical connection 613A. Linkage also comprises a fitting 617A which is rigidly coupled at one of its ends to link 619A and at its opposing end to spherical connection 613A. Linkage 618A comprises six links 619A, 621A, 623A, 625A, 627A and 629A which are interconnected by seven in-plane pivot joints 631A, 633A, 635A, 637A, 639A, 641A and 643A. Link 627A is operationally coupled to a shaft 645A of motor (or other actuator) 647A. Actuator 647A is rigidly coupled to holding mount 632 (not shown in FIG. 7B). When shaft 645A of actuator 647A pivots (i.e. about axis 651A), linkage 618A will pivot into and/or out of the page (i.e. about the axis 651A of link 627A).

FIG. 7B also shows that the axis 651A of link 627A and the axis 653A of link 619A intersect at a point 628A. Spherical support joint 628 is located such that the point 628A of intersection of axes 651A and 653A is coincident with the centre of rotation of spherical support joint 628A. This property of linkage 618A is true for all permitted configurations of linkage 618A and platform 614. Linkages 618B and 618C exhibit similar properties. More specifically, linkage 618B comprises a pair of links 627B, 619B having axes 651B, 653B that intersect at centre of rotation 628A and linkage 618C comprises a pair of links 627C, 619C having axes 651C, 653C that intersect at centre of rotation 628A.

In linkage 618A, links 619A, 621A, 623A, 625A, 627A and 629A are substantially straight, although this is not necessary. In linkage 618A, central links 621A, 625A maybe approximately twice the length of exterior links 619A, 623A, 627A, 629A. Pivot joints 631A, 633A, 635A, 637A, 639A, 641A and 643A of linkage 618A are in-plane pivot joints, which means that their respective pivot axes are parallel with one another. Those skilled in the art will appreciate that sensors (not shown) could be operationally coupled to axis 645A of actuator 647A and/or to one or more of pivot joints 631A, 633A, 635A, 637A, 639A, 641A and 643A and/or to links 619A, 621A, 623A, 625A, 627A and 629A and could be used in conjunction with actuator 647A to provide force-feedback to linkage 618A in a manner similar to that discussed above.

Device 610 comprises three mounts 651A, 651B, 651C (collectively, mounts 651) which are connected to holding mount 632 at one of their ends and which extend away from holding mount 632 toward base surface 653 on which device 610 is standing. Mounts 651, 632 bear the weight of device 610 and hold up device 610 on base surface 653. In device 610 of FIG. 7A, support assembly 624 comprises a support assembly similar to support assembly 24 of device 10 FIGS. 1-3B). More particularly, support assembly 624 comprises: a ball-type spherical joint 628 (see ball 634); a first support member 630 that extends from base surface 653 to ball 634; and a second support member 626 that extends from ball 634 to platform 614. In other respects, device 610 may be substantially similar to any of the force feedback devices discussed above and may have similar variations in respect of the handle assemblies, spherical support joints, and support assemblies as any of the force feedback devices discussed above.

Figure 8:
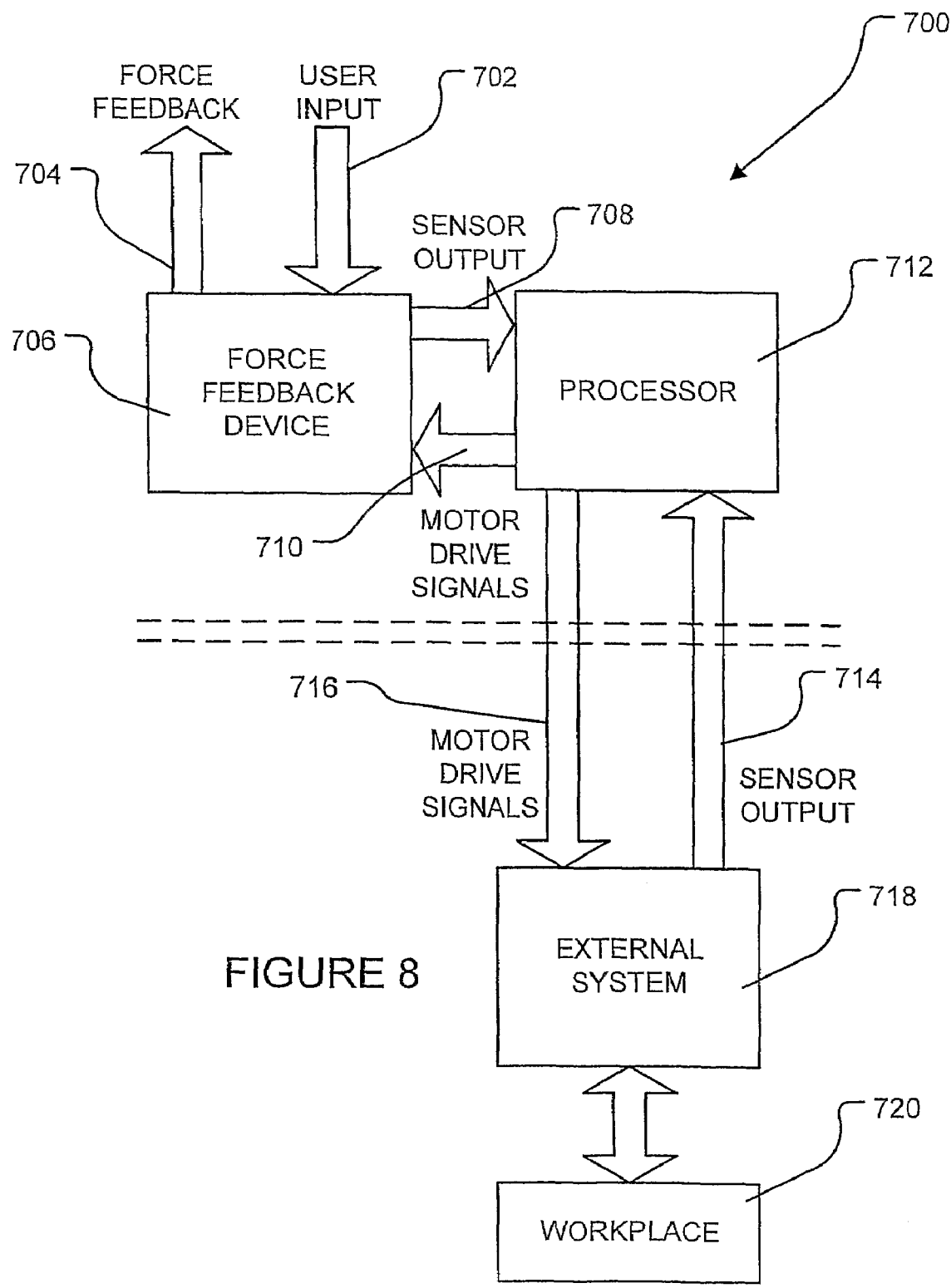
FIG. 8 is a schematic diagram illustrating an application of the devices shown in FIGS. 1-7B in a haptic system.

FIG. 8 is a schematic diagram showing an application of the invention in a haptic system 700. Haptic system 700 represents only one exemplary and non-limiting application of the devices described herein. Those skilled in the art will appreciate that the FIG. 8 diagram is schematic and high-level in nature and that some components of system 700 are omitted for clarity. Haptic system includes a force feedback device 706 which may be implemented in accordance with any of the embodiments described herein. Force feedback device 706 is coupled to a processor 712. In haptic system 700, processor 712 is coupled to an external system 718 that operates in a workplace 720. The objective of haptic system 700 is to permit a user to control the operation of external system 718 in workplace 720 using force feedback device 706. In some alternative applications, external system 718 and workplace 720 can be modeled by processor 712.

A user interacts with force feedback device 702 (e.g. by manipulating a handle assembly) and causes movement of various components of force feedback device 706. For example, a user may cause the platform of device 706 to move in the angular directions θ, φ, ψ as discussed above. The movement of the component(s) of device 706 is detected by sensors and provided as sensor output information 708 to processor 712. Processor 712 is provided with a control model of force feedback device 706 and a control model of external system 718. Using these control models, processor 712 determines motor drive signals 716 that are provided to drive the components of external system 718 and to operate external system 718 in workplace 720.

When external system 718 operates in workplace 720 (i.e. the components of external system 718 move within workplace 720), external system 718 interacts with workplace 720. During such interaction, forces may be applied by workplace 720 to the components of external system 718. For example, external system 718 may be a robot performing a medical procedure on a workplace 720 that is a human patient. One of the components of robot 718 may touch the patient's liver and experience a certain force level and then encounter the patient's rib and experience a different force level.

Such different force levels may manifest themselves as different position responses to motor drive signals 716. For example, if a component of system 718 was moving though liver, then it may move a certain distance in response to a given drive signal level, but when the component encounters bone, it may move much less in response to the same drive signal. These position responses are detected by sensors in external system 718 and are provided to processor 712 as sensor output 714. Using its control models for force feedback device 706 and external system 718, processor determines motor drive signals 710 which are provided to drive the motors of force feedback device 706.

In response to receiving the motor drive signals 710, the motors of force feedback device 706 apply force to the component(s) of force feedback device 706 and thereby provide the user with force feedback 704 as discussed above. This force feedback 704 can enable the user interacting with force feedback device 706 to experience the sensation of "feeling" a virtual object. In the example provided above, the user will experience greater force feedback when external system 718 encounters a patient's bone as opposed to the patient's liver and will therefore "feel" a virtual rib.

It will be appreciated by those skilled in the art that the force feedback 704 provided by system 700 is most useful when the force feedback 704 is provided as quickly as possible and where force feedback device 706 is transparent to the user (i.e. the user feels as though he or she is actually operating external system 718 in workplace 720). As discussed above, the support assembly (including the spherical support joint) of the force feedback devices described herein improves the fidelity and transparency of the force feedback devices.

Where a component (e.g. a motor, actuator, computer, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

In some embodiments of the invention, brakes may be provided to supply force-feedback to a user in addition to or instead of motors. Linear actuators may also be provided in addition to or instead of pivotal actuators.

The handle assemblies described in connection with the devices discussed herein are optional. In alternative embodiments, a user may directly manipulate the platforms of the various devices with some part of the user's body.

The platforms of the force feedback devices disclosed herein need not be solid components. The platforms are preferably something on which a handle assembly can be mounted.

In the illustrated embodiments described herein, spherical joints are implemented using ball and socket joints or 3-DOF joints. Those skilled in the art will appreciate that other embodiments of the invention may make use other spherical joints having the characteristics described above. By way of non-limiting example, a spherical joint having the characteristics discussed above may comprise a first member having a convex surface and a second member having multiple contact points, wherein the multiple contact points are located about an imaginary concave surface, such that the contact points can slideably engage the convex surface of the first member. A portion of the convex surface may be spherically convex and the contact points may be located about an imaginary spherically concave surface. As another non-limiting example, a spherical joint having the characteristics discussed above may comprise a first member having a concave surface and a second member having multiple contact points, wherein the multiple contact points are located about an imaginary convex surface such that the contact points can slideably engage the concave surface of the first member.

The embodiments described above depict devices that can be operated by a user using a single hand. In some embodiments of the invention, a pair of devices (each similar to one of the above-described devices) is provided to be controlled by each of a user's hands.

As discussed above, device 510 of FIG. 6B comprises a spherical joint 528 that is located between platform 514 and handle assembly 512. In device 510, spherical support joint 528 of device 510 comprises a 3-DOF joint 527, such that shaft 550 of handle assembly 512 is capable of projecting through spherical support joint 528. In other embodiments where the spherical support joint is located between the platform and the handle assembly, the shaft of the handle assembly is offset from centre, such that it does not pass through the centre of rotation of the spherical support joint.

Haptic system 700 described above and shown in FIG. 8 incorporates position sensors and make use of position sensor information only. In other embodiments, force feedback device 706 and/or external system 718 may comprise other types of sensors, such as pressure sensors, force sensors and the like which may be used in a manner similar to the position sensors to provide a user with improved force feedback.

In some embodiments, the devices described above can be used as input devices without force feedback. In such cases, the devices described above do not require motors or other actuators for providing force feedback. For example, system 700 of FIG. 8 can be modified such that processor 712 does not provide motor drive signals 710 to device 706.

Haptic system 700 represents only one exemplary and non-limiting application of the devices described herein. In some applications, it is not necessary that processor 712 interact with an external system 718 or a workplace 720. For example, processor 712 may be running a software model or software application, such as a video game. In response to sensor output signals 708, processor 712 may provide motor drive signals 710 on the basis of information and/or instructions obtained from such software.

Accordingly, the scope of the invention is to be construed in accordance with the substance defined by the following claims.

What is claimed is:

1. A user interface system comprising:
   a plurality of linkages connected between a platform and a base, the linkages connected to constrain motion of the platform over at least a portion of a spherical surface;
   a support assembly comprising a spherical joint having a centre of rotation substantially concentric with the spherical surface, the spherical joint acting to constrain motion of the platform to the portion of the spherical surface; and
   a plurality of sensors coupled to detect motion of the platform over the portion of the spherical surface,
   wherein the plurality of linkages comprises three linkages, each of the three linkages comprising: a primary link pivotally coupled to the platform via a primary pivot joint; and a secondary link pivotally coupled to a mount that extends from the base via a secondary pivot joint and pivotally coupled to the primary link via an intermediate pivot joint.

2. A system according to claim 1 comprising a user-manipulable handle coupled to the platform.

3. A system according to claim 2 wherein user manipulation of the handle causes corresponding movement of the platform over the portion of the spherical surface.

4. A system according to claim 2 wherein the user-manipulable handle is moveably coupled to the platform via a longitudinally extending shaft and wherein the user-manipulable handle is moveable relative to the platform in a direction of a longitudinal shaft axis.

5. A system according to claim 4 comprising a handle-position sensor coupled to detect a position of the user-manipulable handle along the longitudinal shaft axis.

6. A system according to claim 5 comprising a handle-position actuator operationally coupled to exert a force which tends to move the user-manipulable handle along the longitudinal shaft axis.

7. A system according to claim 6 comprising a processor configured to:
   receive one or more signals representing the position of the user-manipulable handle along the longitudinal shaft axis from the handle-position sensor;
   determine one or more actuator drive signals representing force feedback based at least in part on the one or more signals from the handle-position sensor; and
   provide the one or more actuator drive signals to the handle-position actuator.

8. A system according to claim 4 wherein the user-manipulable handle comprises one or more finger grips for receiving a user's finger.

9. A system according to claim 8 wherein the one or more finger grips are coupled to a first pivot joint for pivotal movement about a first pivot axis relative to other components of the user-manipulable handle.

10. A system according to claim 9 comprising a first finger-grip sensor coupled to detect an angular position of the finger grips about the first pivot axis.

11. A system according to claim 10 comprising a first finger-grip actuator operationally coupled to exert a torque which tends to pivot the finger grips about the first pivot axis.

12. A system according to claim 11 comprising a processor configured to:
   receive one or more signals representing the angular position of the finger grips about the first pivot axis from the first finger-grip sensor; determine one or more actuator drive signals representing force feedback based at least in part on the one or more signals from the first finger-grip sensor; and provide the one or more actuator drive signals to the first finger-grip actuator.

13. A system according to claim 1 wherein the spherical joint comprises a ball and socket joint, a center of the ball being the centre of rotation.

14. A system according to claim 1 wherein the support assembly comprises at least one first component which extends from the base in a direction toward the platform and at least one second component that extends from the platform in a direction toward the base.

15. A system according to claim 14 wherein one of the first support member and the second support member comprises a convex surface and the other one of the first support member and the second support member comprises a concave surface for slidable movement along the convex surface.

16. A system according to claim 14 wherein the spherical joint comprises a ball located between the at least one first component and the at least one second component and wherein a centre of the ball is the centre of rotation.

17. A system according to 16 wherein the at least one first component comprises a corresponding first concave surface for slidable movement along a surface of the ball and wherein the at least one second component comprises a corresponding second concave surface for slidable movement along a surface of the ball.

18. A system according to claim 16 wherein the ball is rigidly connected to one of: the at least one first component; and the at least one second component;
   and wherein the other one of the at least one first component and the at least one second component comprises a concave surface for slidable movement along a surface of the ball.

19. A system according claim 1 wherein the plurality of sensors comprises at least one sensor corresponding to each of the plurality of linkages, the at least one sensor coupled to sense movement of its corresponding linkage in response to motion of the platform.

20. A system according to claim 19 wherein each linkage comprises at least one corresponding pivot joint and the at least one sensor corresponding to each linkage is coupled to detect an angular configuration of the at least one corresponding pivot joint.

21. A system according to claim 20 comprising a plurality of actuators, the plurality of actuators comprising at least one actuator corresponding to each linkage, the at least one actuator corresponding to each linkage operationally connected to apply torque to the at least one corresponding pivot joint.

22. A system according to claim 21 comprising a processor configured to: receive signals representing position information from the plurality of sensors; determine actuator drive signals representing force feedback based at least in part on the signals representing position information; and provide the actuator drive signals to the at least one actuator corresponding to each of the linkages.

23. A user interface system according to claim 1 comprising an actuator operationally coupled to each of the linkages for providing force feedback with a controllably variable magnitude to the platform.

24. A user interface system according to claim 1 wherein the linkages are configured to establish a plurality of equilibrium positions of the platform.

25. A system according to claim 1 wherein primary axes of the primary pivot joints, secondary axes of the secondary pivot joints and intermediate axes of the intermediate pivot joints intersect at the centre of rotation.

26. A system according to claim 25 comprising at least one actuator corresponding to each of the three linkages, the at least one actuator corresponding to each of the three linkages operationally connected to apply torque to at least one of: the primary pivot joint; the secondary pivot joint; and the intermediate pivot joint.

27. A user interface system comprising:
a plurality of linkages connected between a platform and a base, the linkages connected to constrain motion of the platform over at least a portion of a spherical surface;
a support assembly comprising a spherical joint having a centre of rotation substantially concentric with the spherical surface, the spherical joint acting to constrain motion of the platform to the portion of the spherical surface; and
a plurality of sensors coupled to detect motion of the platform over the portion of the spherical surface;
wherein the plurality of sensors comprises at least one sensor corresponding to each of the plurality of linkages, the at least one sensor coupled to sense movement of its corresponding linkage in response to motion of the platform; and
wherein the plurality of linkages comprises three linkages, each of the three linkages comprising: a primary link pivotally coupled to the platform via a primary pivot joint; and a secondary link pivotally coupled to a mount that extends from the base via a secondary pivot joint and pivotally coupled to the primary link via an intermediate pivot joint.

28. A system according to claim 27 wherein primary axes of the primary pivot joints, secondary axes of the secondary pivot joints and intermediate axes of the intermediate pivot joints intersect at the centre of rotation.

29. A system according to claim 28 wherein the at least one sensor corresponding to each linkage is coupled to detect an angular configuration of at least one of: the primary pivot joint; the secondary pivot joint; and the intermediate pivot joint.

30. A system according to claim 29 comprising at least one actuator corresponding to each of the three linkages, the at least one actuator corresponding to each of the three linkages operationally connected to apply torque to at least one of: the primary pivot joint; the secondary pivot joint; and the intermediate pivot joint.

* * * * *